(12) United States Patent
Otsuka

(10) Patent No.: US 10,309,892 B2
(45) Date of Patent: Jun. 4, 2019

(54) PARTICLE SORTING DEVICE, PARTICLE SORTING METHOD, PROGRAM, AND PARTICLE SORTING SYSTEM

(71) Applicant: Sony Corporation, Tokyo (JP)

(72) Inventor: Fumitaka Otsuka, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/116,830

(22) PCT Filed: Nov. 19, 2014

(86) PCT No.: PCT/JP2014/080588
§ 371 (c)(1),
(2) Date: Aug. 5, 2016

(87) PCT Pub. No.: WO2015/122071
PCT Pub. Date: Aug. 20, 2015

(65) Prior Publication Data
US 2017/0191925 A1     Jul. 6, 2017

(30) Foreign Application Priority Data
Feb. 13, 2014   (JP) .................................. 2014-025156

(51) Int. Cl.
*G01N 15/14*     (2006.01)
*G06T 7/00*     (2017.01)
(Continued)

(52) U.S. Cl.
CPC ..... *G01N 15/1463* (2013.01); *G01N 15/1459* (2013.01); *G06T 7/0012* (2013.01);
(Continued)

(58) Field of Classification Search
CPC ......... G01N 15/1404; G01N 2015/149; G01N 2015/1406; G01N 15/1427;
(Continued)

(56) References Cited

U.S. PATENT DOCUMENTS

| 3,710,933 A | 1/1973 | Fulwyler et al. |
| 3,826,364 A | 7/1974 | Bonner et al. |

(Continued)

FOREIGN PATENT DOCUMENTS

| CN | 1950690 A | 4/2007 |
| EP | 1403633 A2 | 3/2004 |

(Continued)

OTHER PUBLICATIONS

U.S. Appl. No. 13/788,075, filed Mar. 7, 2013, Muraki et al.
(Continued)

*Primary Examiner* — Aklilu K Woldemariam
(74) *Attorney, Agent, or Firm* — Wolf, Greenfield & Sacks, P.C.

(57) ABSTRACT

Disclosed herein are a particle sorting device capable of simply detecting bubbles, foreign substances, or the like in droplets, a method for analyzing particles, a program, and a particle sorting system. The particle sorting device includes a judgment unit, and the judgment unit judges whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

14 Claims, 9 Drawing Sheets

(51) Int. Cl.
  *G06T 7/90* (2017.01)
  *G01N 15/00* (2006.01)
  *G01N 15/10* (2006.01)
  *G01N 35/10* (2006.01)

(52) U.S. Cl.
  CPC ............... *G01N 2015/0011* (2013.01); *G01N 2015/0065* (2013.01); *G01N 2015/1006* (2013.01); *G01N 2015/1068* (2013.01); *G01N 2015/1081* (2013.01); *G01N 2015/149* (2013.01); *G01N 2035/1018* (2013.01); *G06T 7/90* (2017.01)

(58) Field of Classification Search
  CPC ........... G01N 2015/1443; G01N 15/14; G01N 15/1425; G01N 15/1484; G01N 2015/1415; G01N 2015/144; G01N 15/1012; G01N 15/1031; G01N 15/12; G01N 2015/0065; G01N 2015/1081; G01N 2015/0088; G01N 2035/1034; G01N 27/447; G01N 27/44717; G01N 27/44721; G01N 33/543; G01N 35/10; G01N 15/1459; G01N 15/1463; G01N 2015/1006; G01N 21/85; G01N 2021/845; G01N 2021/8592; G01N 21/718; G01N 21/8806; G01N 21/8851; G01N 2201/02; G01N 2201/062; G01N 2201/0621; G01N 15/147; G01N 33/48; G01N 33/5005; G01N 15/1468; G01N 2021/6439; G01N 21/6428; G01N 15/1475; G01N 21/63; C12C 2565/629; C12C 2563/159; C12C 1/686; C12C 2537/143; C12C 1/6827; C12C 2531/113; C12C 2535/131; C12C 1/6874; C12C 1/6816; C12C 1/6806; C12C 1/025; C12C 1/703; C12C 2565/119; C12C 1/68; C12C 2563/149; G06T 7/0012; G06T 7/90; A61M 2205/3306; A61M 2205/50; A61M 5/1689; A61M 5/16886; A61M 2205/3334; A61M 5/1411; A61M 5/16804; A61M 5/16877; A61M 5/172; A61M 5/14228; A61M 2005/16863; A61M 5/16831; A61M 1/3627; C12Q 2565/629; C12Q 2563/159; C12Q 1/686; C12Q 2537/143; C12Q 1/6827; C12Q 2531/113; C12Q 2535/131; C12Q 1/6874; C12Q 1/6816; C12Q 1/6806; C12Q 1/025; C12Q 1/703; C12Q 2565/119; C12Q 1/68; C12Q 2563/149; C12Q 1/02; C12Q 3/00; C12N 5/0612; C12N 5/06; Y10T 436/25
  USPC ........... 382/128, 133; 209/552, 576; 348/61; 436/63, 164
  See application file for complete search history.

(56) References Cited

U.S. PATENT DOCUMENTS

| | | | |
|---|---|---|---|
| 3,924,947 A | 12/1975 | Hogg | |
| 4,009,435 A | 2/1977 | Hogg | |
| 4,168,460 A | 9/1979 | Menke | |
| 4,173,415 A | 11/1979 | Wyatt | |
| 4,284,496 A | 8/1981 | Newton | |
| 4,318,480 A | 3/1982 | Lombardo et al. | |
| 4,318,481 A | 3/1982 | Lombardo et al. | |
| 4,325,483 A | 4/1982 | Lombardo et al. | |
| 4,538,733 A | 9/1985 | Hoffman | |
| 4,616,234 A | 10/1986 | Wint | |
| 4,987,539 A | 1/1991 | Moore et al. | |
| 5,080,770 A | 1/1992 | Culkin | |
| 5,180,065 A | 1/1993 | Touge et al. | |
| 5,483,469 A | 1/1996 | Van den Engh et al. | |
| 5,602,039 A | 2/1997 | Van den Engh | |
| 5,700,692 A | 12/1997 | Sweet | |
| 5,776,781 A | 7/1998 | Vardanega et al. | |
| 6,079,836 A | 6/2000 | Burr et al. | |
| 6,202,734 B1 | 3/2001 | Sackinger et al. | |
| 6,248,590 B1* | 6/2001 | Malachowski | G01N 15/1404 209/127.4 |
| 6,372,506 B1 | 4/2002 | Norton | |
| 6,410,872 B2* | 6/2002 | Campbell | B07C 5/3422 209/576 |
| 6,589,792 B1 | 7/2003 | Malachowski | |
| 6,861,265 B1 | 3/2005 | den Engh | |
| 6,941,005 B2 | 9/2005 | Lary et al. | |
| 6,949,715 B2 | 9/2005 | Kelly | |
| 7,019,293 B1 | 3/2006 | Hamada | |
| 7,024,316 B1* | 4/2006 | Ellison | G01N 15/1459 422/68.1 |
| 7,159,752 B2 | 1/2007 | Farnworth | |
| 7,417,734 B2 | 8/2008 | Kanda | |
| 7,639,358 B2 | 12/2009 | Kanda | |
| 7,691,636 B2 | 4/2010 | Frazier et al. | |
| 7,723,116 B2* | 5/2010 | Evans | C12N 5/0612 422/73 |
| 7,758,811 B2 | 7/2010 | Durack et al. | |
| 7,880,108 B2 | 2/2011 | Schembri et al. | |
| 7,901,947 B2* | 3/2011 | Pollack | G01N 35/10 204/450 |
| 8,246,805 B2 | 8/2012 | Shinoda | |
| 8,570,511 B2 | 10/2013 | Wang | |
| 8,681,335 B2 | 3/2014 | Sharpe et al. | |
| 8,691,584 B2* | 4/2014 | Durack | G01N 33/48 422/73 |
| 8,748,183 B2 | 6/2014 | Durack et al. | |
| 8,883,513 B2* | 11/2014 | Pollack | G01N 35/10 204/450 |
| 8,922,636 B1 | 12/2014 | Belden et al. | |
| 8,922,646 B2 | 12/2014 | Neckels et al. | |
| 9,029,724 B2 | 5/2015 | Hashimoto et al. | |
| 9,087,371 B2 | 7/2015 | Muraki | |
| 9,339,823 B2 | 5/2016 | Muraki et al. | |
| 9,429,276 B2 | 8/2016 | Katsumoto | |
| 9,588,036 B2 | 3/2017 | Shinoda | |
| 9,784,659 B2 | 10/2017 | Tanase et al. | |
| 9,784,660 B2 | 10/2017 | Otsuka et al. | |
| 9,857,286 B2 | 1/2018 | Muraki et al. | |
| 9,958,375 B2 | 5/2018 | Muraki et al. | |
| 10,132,735 B2 | 11/2018 | Muraki | |
| 2002/0171827 A1 | 11/2002 | van den Engh | |
| 2003/0222950 A1 | 12/2003 | Jeanmaire | |
| 2004/0062685 A1 | 4/2004 | Norton et al. | |
| 2004/0086159 A1* | 5/2004 | Lary | G01N 15/1425 382/128 |
| 2006/0125856 A1 | 6/2006 | Kitami et al. | |
| 2006/0177348 A1 | 8/2006 | Yasuda et al. | |
| 2007/0102634 A1 | 5/2007 | Frey et al. | |
| 2007/0195310 A1 | 8/2007 | Kanda | |
| 2007/0257215 A1 | 11/2007 | Rich | |
| 2008/0024619 A1 | 1/2008 | Ono | |
| 2008/0050283 A1 | 2/2008 | Chou et al. | |
| 2008/0053205 A1* | 3/2008 | Pollack | G01N 35/10 73/61.71 |
| 2008/0067068 A1 | 3/2008 | Li | |
| 2008/0092655 A1 | 4/2008 | Takiguchi | |
| 2008/0255705 A1 | 10/2008 | Degeal et al. | |
| 2008/0284827 A1 | 11/2008 | Fagerquist et al. | |
| 2008/0289966 A1 | 11/2008 | Voldman et al. | |
| 2009/0125242 A1 | 5/2009 | Choi et al. | |
| 2009/0170186 A1* | 7/2009 | Wu | B03C 5/026 435/286.1 |
| 2010/0009445 A1 | 1/2010 | Patra et al. | |
| 2010/0118300 A1 | 5/2010 | Wang et al. | |
| 2010/0315639 A1 | 12/2010 | Muraki | |
| 2011/0005931 A1 | 1/2011 | Zhe et al. | |

(56) References Cited

U.S. PATENT DOCUMENTS

| | | | |
|---|---|---|---|
| 2011/0033339 A1 | 2/2011 | Muraki | |
| 2011/0081684 A1 | 4/2011 | Gauer et al. | |
| 2011/0221892 A1 | 9/2011 | Neckels et al. | |
| 2011/0259749 A1 | 10/2011 | Kanda | |
| 2011/0267457 A1* | 11/2011 | Weitz | C12Q 1/6874 348/135 |
| 2011/0275052 A1 | 11/2011 | Schenk et al. | |
| 2011/0284378 A1 | 11/2011 | Shinoda | |
| 2011/0287976 A1 | 11/2011 | Wang et al. | |
| 2012/0076349 A1 | 3/2012 | Manri et al. | |
| 2012/0084022 A1 | 4/2012 | Giovangrandi et al. | |
| 2012/0135874 A1 | 5/2012 | Wang et al. | |
| 2012/0200857 A1 | 8/2012 | Sharpe et al. | |
| 2012/0202237 A1 | 8/2012 | Sedoglavich et al. | |
| 2012/0247231 A1 | 10/2012 | Kery et al. | |
| 2012/0301869 A1 | 11/2012 | Evans | |
| 2012/0314096 A1* | 12/2012 | Kruglick | G06T 19/006 348/222.1 |
| 2013/0188040 A1* | 7/2013 | Kamen | G06F 19/3418 348/135 |
| 2013/0194589 A1* | 8/2013 | Suzuki | G06K 15/1871 358/1.2 |
| 2013/0256136 A1 | 10/2013 | Muraki et al. | |
| 2013/0256197 A1 | 10/2013 | Katsumoto | |
| 2013/0258075 A1 | 10/2013 | Muraki et al. | |
| 2013/0286038 A1 | 10/2013 | Kamath et al. | |
| 2014/0021370 A1* | 1/2014 | Suzuki | G01N 21/6486 250/459.1 |
| 2014/0043436 A1* | 2/2014 | Bell | G06T 19/20 348/46 |
| 2014/0097129 A1 | 4/2014 | Foster et al. | |
| 2014/0144817 A1 | 5/2014 | Hashimoto et al. | |
| 2014/0174206 A1 | 6/2014 | Akiyama et al. | |
| 2014/0193059 A1 | 7/2014 | Muraki | |
| 2014/0212917 A1 | 7/2014 | Durack et al. | |
| 2014/0346047 A1 | 11/2014 | Shinoda | |
| 2014/0354795 A1* | 12/2014 | Tracy | G01P 5/20 348/79 |
| 2015/0068957 A1 | 3/2015 | Otsuka et al. | |
| 2015/0285726 A1 | 10/2015 | Tanase et al. | |
| 2015/0285727 A1 | 10/2015 | Muraki | |
| 2016/0148433 A1* | 5/2016 | Petrovskaya | G06T 19/006 345/633 |
| 2016/0223451 A1 | 8/2016 | Muraki et al. | |
| 2016/0245736 A1 | 8/2016 | Muraki et al. | |
| 2016/0266027 A1 | 9/2016 | Muraki et al. | |
| 2017/0191925 A1* | 7/2017 | Otsuka | G01N 15/1459 |
| 2017/0241889 A1 | 8/2017 | Otsuka et al. | |
| 2018/0058999 A1 | 3/2018 | Otsuka et al. | |
| 2018/0188150 A1 | 7/2018 | Muraki et al. | |
| 2018/0313740 A1 | 11/2018 | Otsuka | |

FOREIGN PATENT DOCUMENTS

| | | |
|---|---|---|
| GB | 1 103 190 A | 2/1968 |
| JP | 53-013263 | 2/1978 |
| JP | 56-030870 A | 3/1981 |
| JP | 62-036542 A | 2/1987 |
| JP | 62-167478 A | 7/1987 |
| JP | 64-012245 A | 1/1989 |
| JP | 09-189653 A | 7/1997 |
| JP | 10-507525 A | 7/1998 |
| JP | 11-501258 A | 2/1999 |
| JP | 2002-505423 A | 2/2002 |
| JP | 2002-521658 A | 7/2002 |
| JP | 2004-257756 A | 9/2004 |
| JP | 2005-315799 A | 11/2005 |
| JP | 2006-504970 A | 2/2006 |
| JP | 2006-242849 A | 9/2006 |
| JP | 2006-292769 A | 10/2006 |
| JP | 2007-532874 A | 11/2007 |
| JP | 2008-107110 A | 5/2008 |
| JP | 2009-145213 A | 7/2009 |
| JP | 2009-198511 A | 9/2009 |
| JP | 2009-298012 A | 12/2009 |
| JP | 2010-510782 A | 4/2010 |
| JP | 2010-190680 A | 9/2010 |
| JP | 2010-216992 A | 9/2010 |
| JP | 2010-286292 A | 12/2010 |
| JP | 2010-286341 A | 12/2010 |
| JP | 2011-033598 A | 2/2011 |
| JP | 4805417 B1 | 2/2011 |
| JP | 2011-509075 A | 3/2011 |
| JP | 2011-232033 A | 11/2011 |
| JP | 2011-237201 A | 11/2011 |
| JP | 2012-047464 A | 3/2012 |
| JP | 2013-210264 A | 10/2013 |
| JP | 2013-210270 A | 10/2013 |
| JP | 2015-152439 A | 8/2015 |
| WO | WO 2001/002836 A1 | 1/2001 |
| WO | WO 2010/095391 A1 | 8/2010 |
| WO | WO 2010/129787 A2 | 11/2010 |
| WO | WO 2010/140460 A1 | 12/2010 |
| WO | WO 2013/145905 A1 | 10/2013 |
| WO | WO 2014/115409 A1 | 7/2014 |

OTHER PUBLICATIONS

U.S. Appl. No. 13/788,165, filed Mar. 7, 2013, Muraki et al.
U.S. Appl. No. 14/118,788, filed Nov. 19, 2013, Muraki.
U.S. Appl. No. 14/118,994, filed Nov. 20, 2013, Hashimoto et al.
U.S. Appl. No. 14/386,368, filed Sep. 19, 2014, Otsuka et al.
U.S. Appl. No. 14/440,765, filed May 5, 2015, Tanase et al.
U.S. Appl. No. 14/737,370, filed Jun. 11, 2015, Muraki.
U.S. Appl. No. 15/028,411, filed Apr. 8, 2016, Muraki et al.
U.S. Appl. No. 15/028,419, filed Apr. 8, 2016, Muraki et al.
U.S. Appl. No. 15/093,879, filed Apr. 8, 2016, Muraki et al.
U.S. Appl. No. 15/506,497, filed Feb. 24, 2017, Otsuka et al.
U.S. Appl. No. 15/687,948, filed Aug. 28, 2017, Otsuka et al.
U.S. Appl. No. 15/907,805, filed Feb. 28, 2018, Muraki et al.
Chinese Office Action and English translation thereof dated Mar. 3, 2016 in connection with Chinese Application No. 2013100954250.
Japanese Office Action dated Feb. 23, 2016 in connection with Japanese Application 2012-246432 and English translation thereof.
International Preliminary Report on Patentability and English translation thereof dated Aug. 25, 2016 in connection with Application No. PCT/JP2014/080588.
International Preliminary Report on Patentability and English translation thereof dated May 3, 2018 in connection with International Application No. PCT/JP2016/070938.
Hartman et al., Jet break-up in electrohydrodynamic atomization in the cone-jet mode. J. Aerosol Sci. vol. 31(1), pp. 65-95; Mar. 1999.
Orme et al., Electrostatic charging and deflection of nonconventional droplet streams formed from capillary stream breakup. Phys. Fluids. vol. 12(9); Sep. 2000; pp. 2224-2235.
Yoon et al., 3D particle position and 3D velocity field measurement in microvolume via the defocusing concept. Meas. Sci. Technol. 17 (2006) 2897-2905.
Morton et al., Hydrodynamic metamaterials: Microfabricated arrays to steer, refract, and focus streams of biomaterials. PNAS May 27, 2008. vol. 105(21); 7434-7438.
Luo et al., Three-dimensional tracking of fluorescent particles applied to micro-fluidic measurements. 2006. J. Micromech. Microeng. vol. 16; 1689-1699.
U.S. Appl. No. 15/767,426, filed Apr. 11, 2018, Otsuka.
International Search Report and Written Opinion dated Jan. 8, 2015 in connection with International Application No. PCT/JP2014/005167.
International Preliminary Report on Patentability dated Apr. 28, 2016 in connection with International Application No. PCT/JP2014/005167.
International Search Report and Written Opinion and English translation thereof dated Nov. 18, 2014 in connection with International Application No. PCT/JP2014/074610.
International Preliminary Report on Patentability and English translation thereof dated Apr. 28, 2016 in connection with International Application No. PCT/JP2014/074610.

(56) References Cited

OTHER PUBLICATIONS

International Search Report and English translation thereof dated Sep. 27, 2016 in connection with International Application No. PCT/JP2016/070938.
International Search Report and Written Opinion dated Nov. 6, 2015 in connection with International Application No. PCT/JP2015/004282.
International Preliminary Report on Patentability dated Mar. 16, 2017 in connection with International Application No. PCT/JP2015/004282.
International Search Report and Written Opinion and English translation thereof dated Feb. 24, 2015 in connection with International Application No. PCT/JP2014/080588.
Japanese Office Action and English translation thereof dated Dec. 15, 2015 in connection with Japanese Application No. 2012-080366.
Chinese Office Action and English translation dated issued Mar. 3, 2016 in connection with Chinese Application No. 2013100954250.
International Search Report and Written Opinion dated Mar. 11, 2014 in connection with International Application No. PCT/JP2013/005910.
International Preliminary Report on Patentability dated May 21, 2015 in connection with International Application No. PCT/JP2013/005910.
Japanese Office Action dated Feb. 23, 2016 in connection with Japanese Application No. 2012-246432 and English translation thereof.
International Search Report and English translation thereof dated Mar. 12, 2013 in connection with Application No. PCT/JP2013/053324.
International Preliminary Report on Patentability and English translation thereof dated Oct. 9, 2014 in connection with Application No. PCT/JP2013/053324.
Extended European Search Report dated Aug. 26, 2014 in connection with Application No. 13768656.4.
International Search Report and Written Opinion and English translation thereof dated Mar. 5, 2013 in connection with Application No. PCT/JP2013/052467.
Japanese Office Action dated Jul. 15, 2014 and English translation thereof in connection with Application No. 2013-547043.
International Search Report and Written Opinion and English translation thereof dated Mar. 5, 2013 in connection with Application No. PCT/JP2013/051800.
International Search Report and Written Opinion and English translation thereof dated Jan. 21, 2014 in connection with Application No. PCT/JP2013/081152.
International Preliminary Report on Patentability and English translation thereof dated Oct. 9, 2014 in connection with Application No. PCT/JP2013/051800.
Chinese Office Action dated Aug. 25, 2015 in connection with Chinese Application No. 2013800154978 and English translation thereof.
Extended European Search Report dated Sep. 23, 2016 in connection with European Application No. 13872550.2.
International Preliminary Report on Patentability and English translation thereof dated Aug. 6, 2015 in connection with Application No. PCT/JP2013/081152.
International Preliminary Report on Patentability and English translation thereof dated Aug. 25, 2016 in connection with International Application No. PCT/JP2014/080588.
Bonner et al., Flourescence Activated Cell Sorting. Review of Scientific Instruments. Mar. 1972; 43(3):404-9.
McIntyre et all., Quantitative Slm-based differential interference contrast imaging. Optics Express. Jun. 2010; 18(13):14063-78.
Murphy et al., Differential Interference Contrast, Olympus Microscopy Resource Center, https://web.archive.org/web/20030312041453/http://www.olympusmicro.com:80/primer/techniques/dic/dichome.html, retrieved from the WayBack Machine on Mar. 30, 2018, noting date of Mar. 12, 2003, 3 pages.
No Author Listed, The EPICS® ALTRA™ Flow Cytometer, Sorting Tutorial, Jul. 1, 2000, Coulter International Corporation, 47 pages.
Shapiro, HM, Chapter 6: Flow Sorting, Practical Flow Cytometry, 4th Edition, Dec. 31, 2003, pp. 257-271.
Yoshimura et al., The Latest Technology [Modern Technology] of a Cell Sorter, Applied Research Report, Jasco Report. 1990;32(1):1-20.
Written Opinion and English translation thereof dated Sep. 27, 2016 in connection with International Application No. PCT/JP2016/070938.

\* cited by examiner

PARTICLE SORTING DEVICE, PARTICLE SORTING METHOD, PROGRAM, AND PARTICLE SORTING SYSTEM

CROSS-REFERENCE TO RELATED APPLICATIONS

This application is a National Stage of International Application No. PCT/JP2014/080588, filed in the Japanese Patent Office as a Receiving office on Nov. 19, 2014, which claims priority to Japanese Patent Application Number 2014-025156, filed in the Japanese Patent Office on Feb. 13, 2014, each of which is hereby incorporated by reference in its entirety.

TECHNICAL FIELD

The present technology relates to a particle sorting device, a particle sorting method, a program thereof, and a particle sorting system. More specifically, the present technology relates to a technique for detecting the presence or absence of bubbles, foreign substances, or the like in droplets based on an image of the droplets.

BACKGROUND ART

Flow cytometry (flow cytometer) is generally used to analyze cells, microorganisms, and biologically-relevant particles such as liposomes (see, for example, Non-Patent Document 1). Flow cytometry is a process in which particles passing through a flow channel in a line are analyzed one by one by detecting fluorescence or scattered light emitted from each of the particles irradiated with laser light (exciting light) of a specific wavelength. Such flow cytometry can determine the type, size, and structure of individual particles by converting light detected by a photodetector into digitized electric signals and performing statistical analysis.

Some flow cytometers have the function of sorting and recovering only microparticles having specific characteristics based on the result of analysis. Particularly, a microparticle sorting device intended to sort cells is called "cell sorter". In the cell sorter, a vibration is generally applied to a flow cell or microchip by a vibrating element or the like to convert a fluid discharged from a flow channel thereof into droplets (see Patent Documents 1 and 2).

In the cell sorter, the entry of bubbles, foreign substances, or the like into a sheath line or sample line disrupts a laminar flow or droplets, which leads to a reduction in the reliability of analysis data or a reduction in sorting accuracy and sorting purity. For example, Patent Document 3 discloses a technique about a cell sorter equipped with a bubble detector. According to this technique, bubbles present in a flow channel can be detected by a bubble detector connected to the flow channel.

CITATION LIST

Patent Documents

Patent Document 1: Japanese Translation of PCT Application No. 2007-532874
Patent Document 2: Japanese Patent Application Laid-Open No. 2010-190680
Patent Document 3: US Patent Application Laid-Open No. 2007/0257215

Non-Patent Document

Non-Patent Document 1: "Separate Volume of Cell Technology, Experimental Protocol Series, Master of Flow Cytometry", Second Edition, edited by Hiromitsu Nakauchi, published by Shuujunsha on Aug. 31, 2006

SUMMARY OF THE INVENTION

Problems to be Solved by the Invention

However, the particle sorting device disclosed in Patent Document 3 needs to have the bubble detector inside thereof, which increases the cost of the device and limits the structural freedom of the device. Further, there has been a demand that foreign substances or the like as well as bubbles be able to be detected.

It is therefore a major object of the present disclosure to provide a particle sorting device capable of simply detecting bubbles, foreign substances, or the like in droplets, a particle sorting method, a program, and a particle sorting system.

Solutions to Problems

The present disclosure provides a particle sorting device including a judgment unit that judges whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

The reference image information may include the reference droplet image information and reference background image information about a brightness of an image of a background other than the droplets, whose peak brightness value is higher than that of the reference droplet image information, and the captured image information may include the captured droplet image information and captured background image information about a brightness other than the droplets, whose peak brightness value is higher than that of the captured droplet image information.

Further, the judgment unit may judge whether or not the peak brightness value of the captured droplet image information is higher than the peak brightness value of the reference droplet image information.

Further, the judgment unit may judge whether or not the captured droplet image information is smaller in a number of pixels within a predetermined range of brightness from the peak brightness value of the droplet image in the reference droplet image information than the reference droplet image information.

Further, the judgment unit may judge whether or not the captured droplet image information is smaller in a number of pixels within a predetermined range of brightness from the peak brightness value of the image other than the droplets in the reference image information than the reference droplet image information.

Further, the particle sorting device may include a charge unit that applies an electric charge to at least some of droplets discharged from the orifice, deflection plates that are provided so as to be opposed to each other across a fluid stream formed by the droplets to change a traveling direction of the droplets, and a first imaging unit that captures an image of the droplets at a position where a fluid discharged from the orifice is converted into droplets to generate the reference image information and the captured image information.

In this case, the particle sorting device may further include a storage unit that stores the reference image information.

Further, the reference image information may be image information including an image of droplets containing no particle.

Further, the particle sorting device may further include a second imaging unit that captures an image of the droplets that have passed through between the deflection plates, wherein the judgment unit may judge whether or not second image information of the droplets acquired by the second imaging unit is previously-set stable image information, and wherein when the second image information is the stable image information, image information of the droplets about the second image information captured by the first imaging unit may be determined as the reference image information.

Further, the particle sorting device may further include a notification unit that notifies a user of warning information when the captured image information has changed with respect to the reference image information.

Further, the particle sorting device may further include a control unit that automatically stops sorting of particle-containing droplets when the captured image information has changed with respect to the reference image information.

The present disclosure also provides a method for sorting particles, including the step of allowing a judgment unit to judge whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

The present disclosure also provides a program which allows a particle sorting device to perform a function of judging whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

The present disclosure also provides a particle sorting system including a judgment unit that judges whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

Effects of the Invention

According to the present disclosure, it is possible to simply detect bubbles, foreign substances, or the like in droplets. It is to be noted that the effect described here is merely illustrative, and the effect of the present technology is not limited thereto, and may be any one of the effects described in this disclosure.

MODES FOR CARRYING OUT THE INVENTION

Hereinbelow, embodiments for carrying out the present disclosure will be described in detail with reference to the accompanying drawings. It is to be noted that the present disclosure is not limited to the following embodiments. The embodiments will be described in the following order.

1. First Embodiment
(An example of a sorting device that detects bubbles, foreign substances, or the like based on previously-stored reference image information)

2. Second Embodiment
(An example of a sorting device that uses, as reference image information, image information of non-particle-containing droplets containing no particle)

3. Third Embodiment
(An example of a sorting device that determines reference image information from image information of a side stream)

4. Fourth Embodiment
(An example of a system in which particle sorting and detection of bubbles, foreign substances, or the like in droplets are performed by different devices)

<1. First Embodiment>

Figure 1:
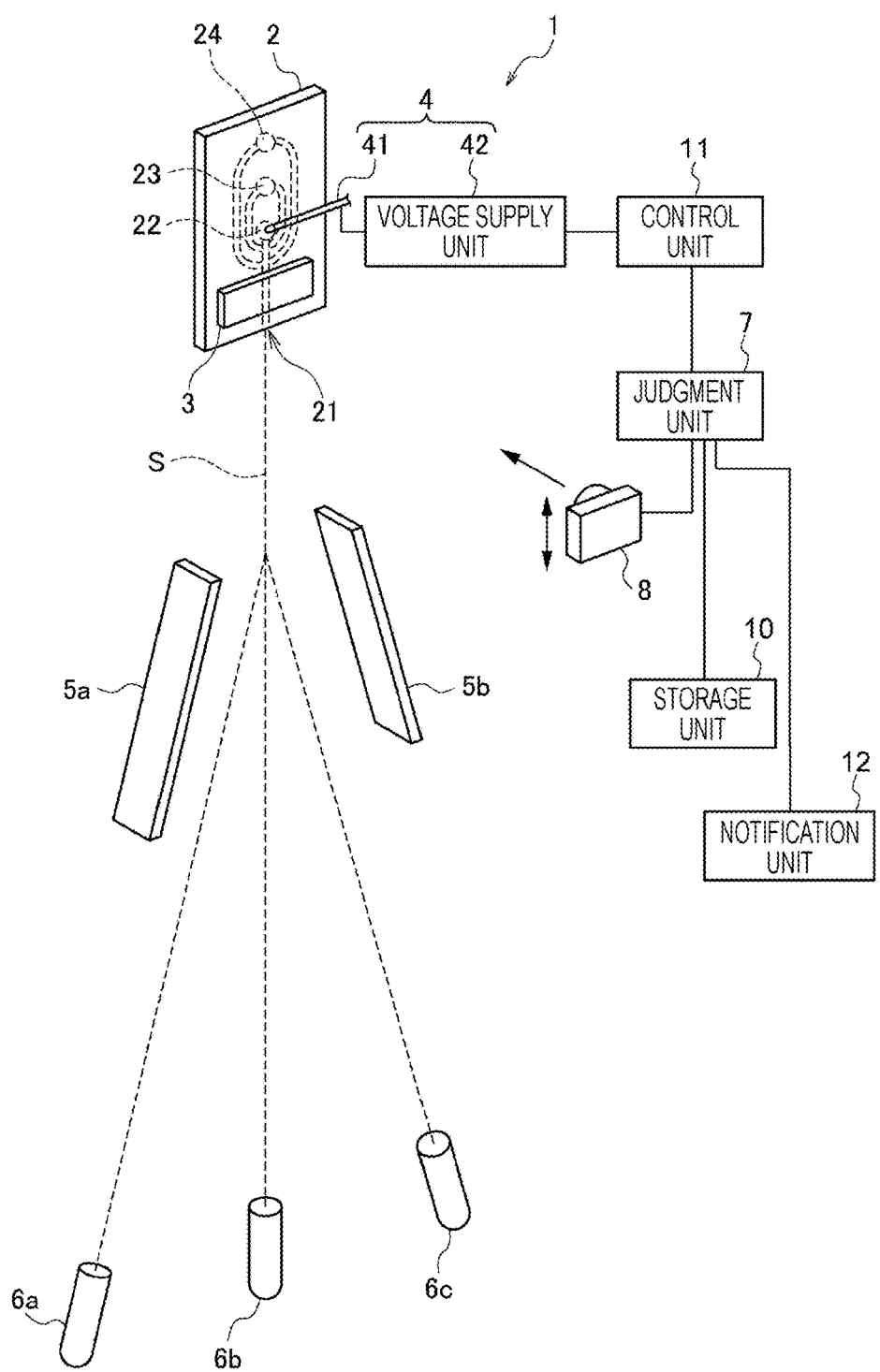
FIG. 1 is a schematic view showing an example of the structure of a particle sorting device 1 according to a first embodiment of the present disclosure.

First, a particle sorting device 1 according to a first embodiment of the present disclosure will be described. FIG. 1 is a schematic view showing the structure of the particle sorting device 1 according to the first embodiment of the present disclosure.

[Overall Structure of Device]

The particle sorting device 1 according to this embodiment is intended to detect bubbles, foreign substances, or the like in particle-containing droplets based on the information of a captured image, and as shown in FIG. 1, includes a microchip 2, a vibrating element 3, a charge unit 4, deflection plates 5a and 5b, a judgment unit 7, a storage unit 10, etc.

[Particles]

Particles to be analyzed and sorted by the particle sorting device 1 according to this embodiment widely include cells, microorganisms, biologically-relevant microparticles such as ribosomes, and synthetic particles such as latex particles, gel particles, and industrial particles.

Examples of the biologically-relevant microparticles include chromosomes, ribosomes, mitochondria, and organelles (cell organelles) that constitute various cells. Examples of the cells include plant cells, animal cells, and blood cells. Examples of the microorganisms include bacteria such as *Escherichia coli*, viruses such as tobacco mosaic viruses, and fungi such as yeasts. The biologically-relevant microparticles may include also biologically-relevant polymers such as nucleic acids, proteins, and complexes thereof.

On the other hand, examples of the industrial particles include those made of an organic polymer material, an inorganic material, or a metal material. Examples of the organic polymer material to be used include polystyrene, styrene-divinyl benzene, and polymethyl methacrylate. Examples of the inorganic material to be used include glass, silica, and magnetic materials. Examples of the metal material to be used include gold colloids and aluminum. It is to be noted that these particles generally have a spherical shape, but may have a non-spherical shape, and the size or mass thereof is not particularly limited, either.

[Microchip 2]

The microchip 2 includes a sample inlet 22 into which a liquid containing particles to be sorted (sample liquid) is introduced, a sheath inlet 23 into which a sheath liquid is introduced, and a suction outlet 24 for eliminating obstructions or bubbles. In the microchip 2, the sample liquid is introduced into the sample inlet 22, joined with the sheath liquid introduced into the sheath inlet 23, sent to a sample flow channel, and discharged from an orifice 21 provided at the end of the sample flow channel.

Further, the sample flow channel is connected to a suction flow channel communicating with the suction outlet 24. The suction flow channel is intended to eliminate obstructions or bubbles. More specifically, when obstructions or bubbles appear in the sample flow channel, a negative pressure is formed in the sample flow channel to temporarily reverse the flow in the sample flow channel. The suction outlet 24 is connected to a negative-pressure source such as a vacuum pump.

The microchip 2 may be made of glass or any plastic (PP, PC, COP, PDMS). The microchip 1 is preferably made of a material that is permeable to measuring light emitted from a photodetector that will be described later, that shows little autofluorescence, and that has a small optical error due to a small wavelength dispersion.

The microchip 2 may be formed by wet etching or dry etching of a glass substrate or by nanoimprinting, injection molding, or mechanical processing of a plastic substrate. The microchip 2 may be formed by, for example, sealing a substrate having a sample flow channel formed therein with a substrate made of the same or a different material.

[Vibrating Element 3]

The vibrating element 3 is intended to apply a micro vibration to a liquid flowing through a flow channel to convert a fluid discharged from the orifice 21 into droplets to create a fluid stream (flow of droplets) S. The vibrating element 3 to be used may be a piezoelectric element or the like. The vibrating element 3 may be provided at a position where a vibration can be applied to a liquid flowing through a flow channel. For example, the vibrating element 3 may be provided inside the microchip 2, or may be provided so as to abut on the microchip 2, or may be attached to a tube for introducing a liquid into a flow channel, such as a sheath tube.

[Charge Unit 4]

The charge unit 4 is intended to apply a positive or negative electric charge to the droplets discharged from the orifice 21, and includes an electrode 41 for charging and a voltage source (voltage supply unit 42) that applies a predetermined voltage to the electrode 41. The electrode 41 for charging is provided so as to come in contact with the sheath liquid and/or the sample liquid flowing through a flow channel to apply an electric charge to the sheath liquid and/or the sample liquid. For example, the electrode 41 for charging is inserted into a charging electrode inlet of the microchip 2.

It is to be noted that in FIG. 1, the electrode 41 for charging is provided so as to come in contact with the sample liquid, but the present disclosure is not limited thereto. The electrode 41 for charging may be provided so as to come in contact with the sheath liquid or may be provided so as to come in contact with both the sample liquid and the sheath liquid. However, the electrode 41 for charging is preferably provided so as to come in contact with the sheath liquid in consideration of an influence on cells to be sorted.

By electrically charging desired droplets by the application of a positive or negative electric charge in such a manner as described above, arbitrary droplets can be separated by an electric force. Further, only arbitrary droplets can be electrically charged by synchronizing the timing of charging by the charge unit 4 with the supply of voltage to the vibrating element 3.

[Deflection Plates 5a and 5b]

The deflection plates 5a and 5b are provided so as to be opposed to each other across the fluid stream S to change the travelling direction of each of the droplets in the fluid stream S by an electric force exerted between the deflection plates and an electric charge applied to the droplet so that the droplets are guided to predetermined recovery containers 6a to 6c. These deflection plates 5a and 5b to be used may be, for example, commonly-used electrodes.

Different positive and negative voltages are applied to the deflection plates 5a and 5b, respectively to generate an electric field. When the charged droplets pass through the electric field, an electric force (Coulomb force) is generated so that each of the droplets is attracted toward either of the deflection plates 5a and 5b. The particle sorting device 1 can control the direction of the flow of droplets (side stream) attracted by the electric field by changing the polarity (positive or negative) or amount of electric charges applied to the droplets, which makes it possible to simultaneously sort a plurality of mutually different particles.

[Recovery Containers 6a to 6c]

The recovery containers 6a to 6c are intended to recover the droplets that have passed through between the deflection plates 5a and 5b. The recovery containers 6a to 6c for experimental use may be general-purpose plastic tubes or glass tubes. These recovery containers 6a to 6c are preferably replaceably provided in the device. When receiving non-target particles, one or two of the recovery containers 6a to 6c may be connected to a flow channel for discharging recovered droplets.

It is to be noted that the number or type of recovery containers provided in the particle sorting device 1 is not particularly limited. Further, when three or more recovery containers are provided, each of the droplets may be guided to and recovered in any one of the recovery containers based on the presence or absence of an electric force exerted between the droplet and the deflection plates 5a and 5b and the magnitude of the electric force.

[Judgment Unit 7]

The judgment unit 7 judges whether or not captured image information 81 has changed with respect to reference image information 80. As will be described later, the reference image information 80 is image information including reference droplet image information 801 acquired by capturing an image of droplets not containing bubbles, foreign substances, or the like after discharge from the orifice. The captured image information 81 is image information including captured droplet image information 811 about the brightness of an image of particle-containing droplets.

When the judgment unit 7 judges that the captured image information 81 has changed with respect to the reference image information 80, it is apparent that bubbles, foreign substances, or the like are contained in the particle-containing droplets. Therefore, when bubbles, foreign substances, or the like are contained, sorting can be stopped to maintain the stability or reliability of the device.

[First Imaging Unit (Camera) 8]

A first imaging unit (camera) 8 captures an image of the droplets at a position where a fluid discharged from the orifice is converted into droplets (break-off point) to generate the reference image information 80 and the captured image information 81. It is to be noted that an image of the droplets can be captured not only by an imaging device such as a CCD or CMOS camera but also by any imaging element such as a photoelectric conversion element. The first imaging unit 8 may have a moving system for changing its position. The particle sorting device 1 according to this embodiment may include not only the first imaging unit 8 but also a light source (not shown) that illuminates an imaging region. By allowing the first imaging unit 8 to emit strobe light for a certain period of time every droplet-forming cycle, a droplet image can be captured at a specific timing when a droplet is formed.

[Storage Unit 10]

The storage unit 10 is a device for storing various data, and includes, for example, a magnetic-storage device such as a hard disk drive (HDD), a semiconductor storage device, an optical storage device, or a magneto-optical storage device. The storage unit 10 stores image information acquired by the first imaging unit 8 through an input-output interface. Particularly, as will be described later, the storage unit 10 may previously store the reference image information 80.

[Control Unit 11]

A control unit 11 can control the particle sorting device 1 to automatically stop the sorting of particle-containing droplets when the captured image information 81 has changed with respect to the reference image information 80. A user can arbitrarily set in advance whether or not to allow the control unit 11 to perform this function.

[Notification Unit 12]

A notification unit 12 notifies a user of warning information when the captured image information 81 has changed with respect to the reference image information 80. This warning information is not particularly limited as long as a user can understand that bubbles, foreign substances, or the like are contained in the droplets. For example, the warning information may be displayed information such as flashing of a lamp provided in the particle sorting device 1 or output information such as an audible alarm.

[Light Detection Unit]

The particle sorting device 1 according to this embodiment further includes, for example, a light detection unit (not shown) that irradiates a predetermined area in the sample flow channel with light (measuring light) and detects light (light to be measured) emitted from particles flowing through the sample flow channel. The light detection unit may be configured in the same manner as that used in conventional flow cytometry. More specifically, the light detection unit includes a laser light source, an irradiation system including a condenser lens that condenses laser light and irradiates particles with the laser light, a dichroic mirror, and a band-pass filter, and a detection system that detects light to be measured emitted from the particles irradiated with the laser light.

The detection system includes, for example, a photo multiplier tube (PMT) or an area imaging element such as a CCD or CMOS element. It is to be noted that the irradiation system and the detection system may be configured to use the same optical path or separate optical paths. Further, the light to be measured detected by the detection system of the light detection unit is light emitted from the particles irradiated with the measuring light, and may be, for example, any scattered light such as forward-scattered light, side-scattered light, Rayleigh scattering, or Mie scattering or fluorescence.

[Operation]

Hereinbelow, a description will be made about the operation of the particle sorting device 1 according to this embodiment, that is, a method for detecting bubbles, foreign substances, or the like in droplets of a sample containing particles with the use of the particle sorting device 1.

Figure 2:
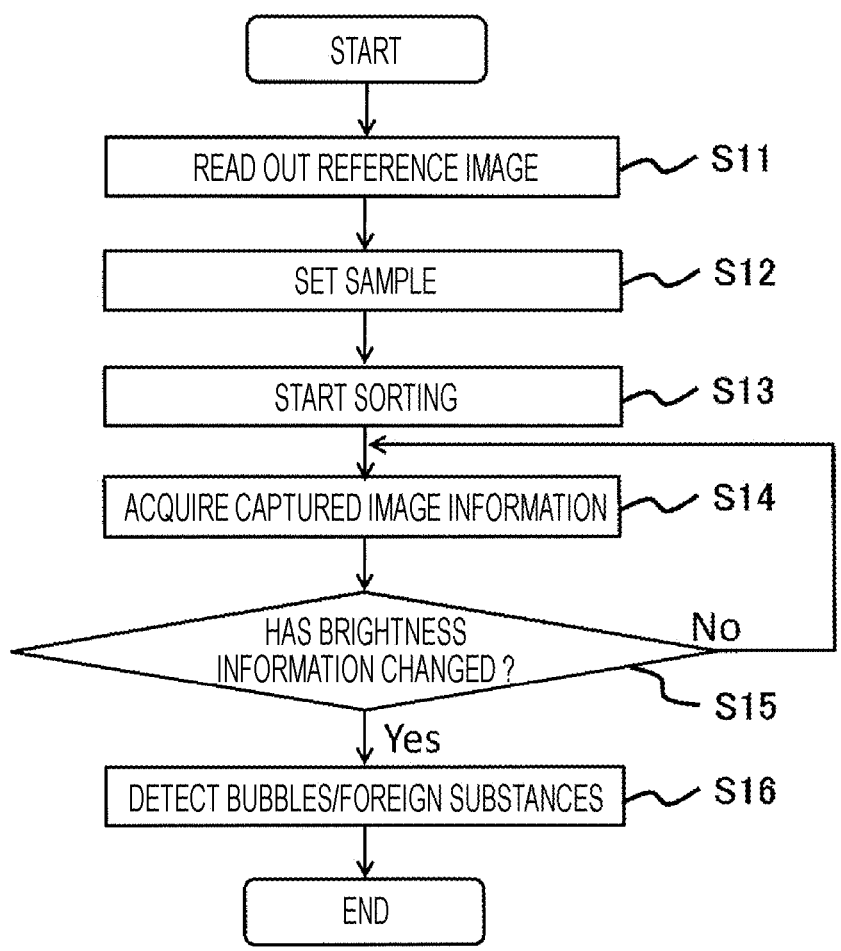
FIG. 2 is a flow chart showing the summary of a method for detecting bubbles, foreign substances, or the like with the use of the particle sorting device 1 according to this embodiment.

FIG. 2 is a flow chart showing the summary of a method for detecting bubbles, foreign substances, or the like with the use of the particle sorting device 1 according to this embodiment. First, the reference image information 80 is read out from the storage unit 10 (Step S11).

Figure 3:
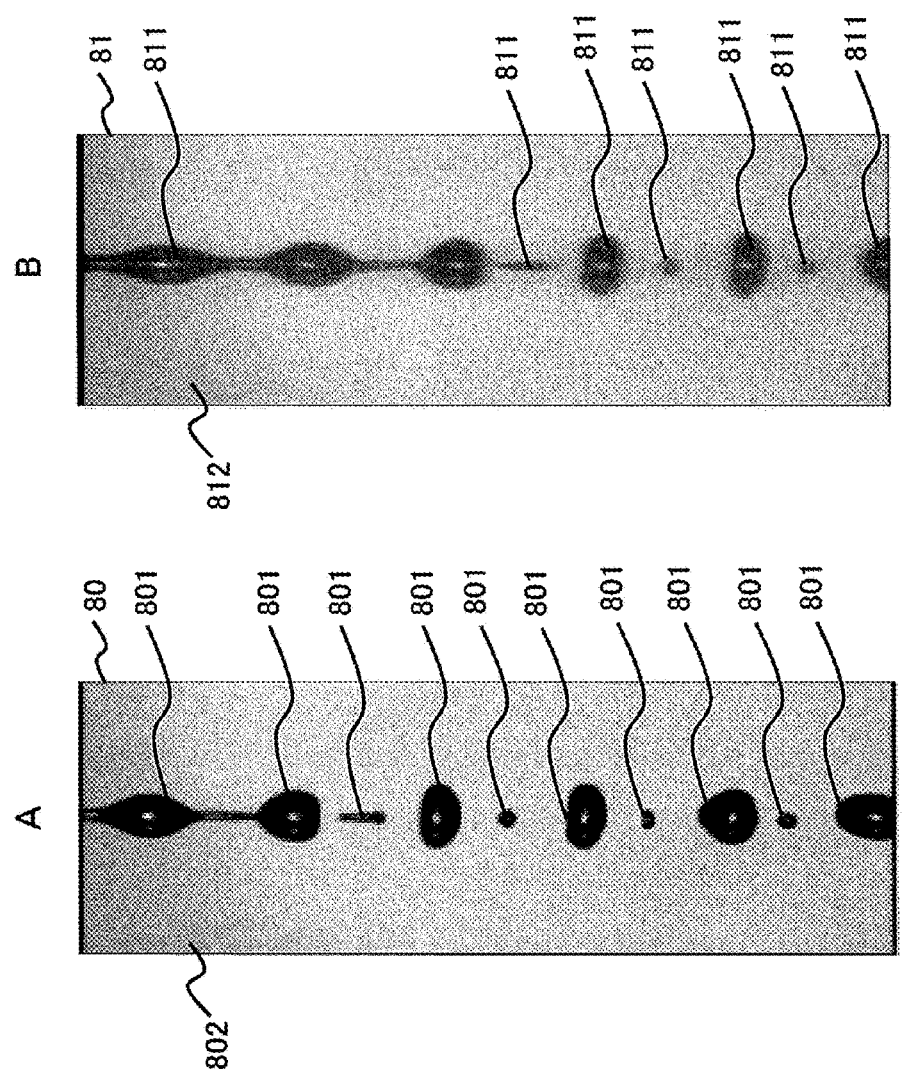
FIGS. 3A and 3B show examples of images captured by a first imaging unit 8.

FIG. 3 shows examples of images captured by the first imaging unit 8, wherein FIG. 3A is an image concerning the reference image information 80 and FIG. 3B is an image concerning the captured image information 81 that will be described later. The reference image information 80 is previously-set image information including reference droplet image information 801 about the brightness of an image of droplets captured after discharge from the orifice 21, that is, image information including droplets not containing bubbles, foreign substances, or the like. It is to be noted that reference sign 802 denotes reference background image information about an image of a background other than the droplets. It is to be noted that the frequency of droplet formation is 10 to 30 kHz, and the first imaging unit 8 operates at about 30 fps, and therefore each of the images shown in FIG. 3 is obtained by overlaying several hundred to several thousand images.

Then, a sample is set in the particle sorting device 1 to start sorting of droplets (Steps S12 and S13 in FIG. 2). Then, droplets are imaged by the first imaging unit 8 to acquire captured image information 81 of such an image as shown in FIG. 3B (Step S14).

Figure 4:
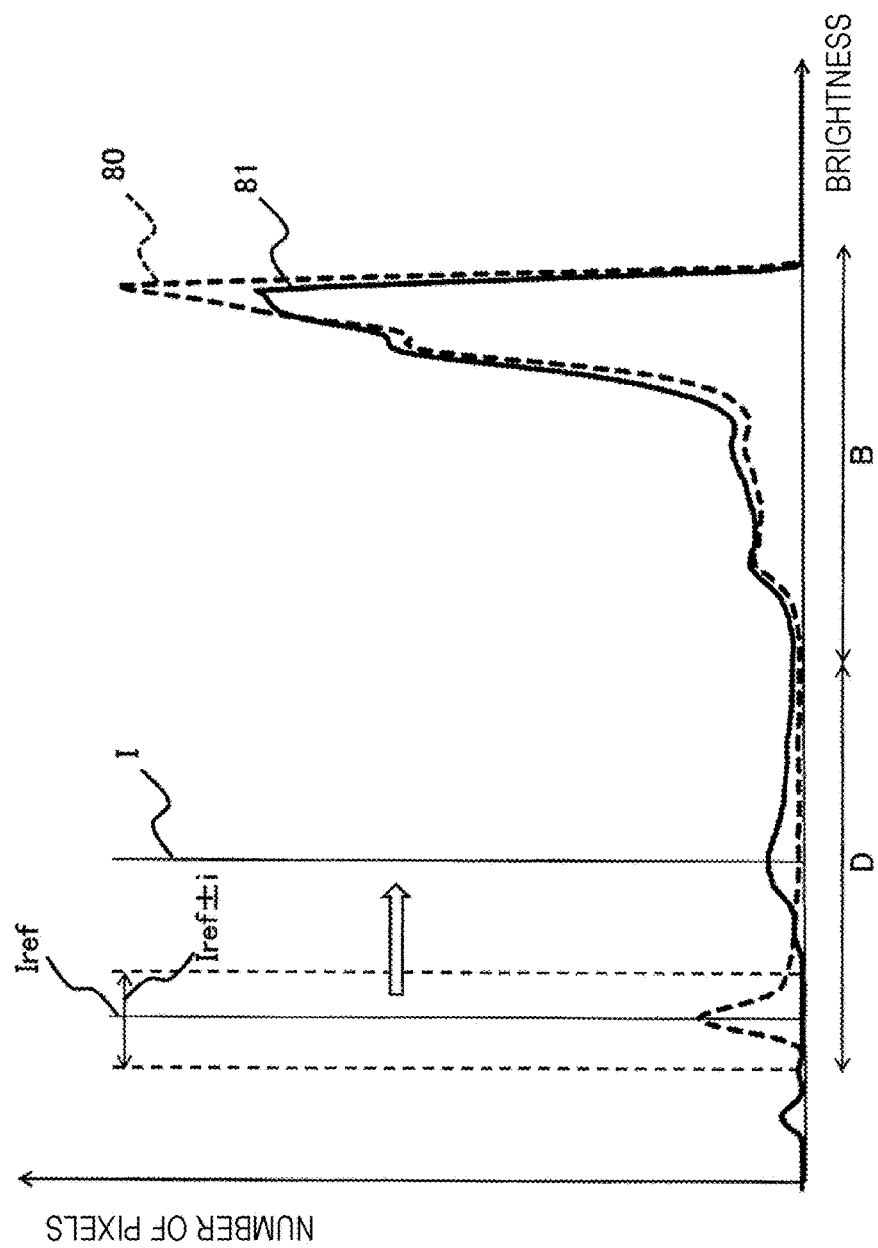
FIG. 4 shows an example of a histogram about reference image information 80 and captured image information 81.

Then, the judgment unit 7 judges whether or not the captured image information 81 has changed with respect to the reference image information 80 (Step S15). FIG. 4 shows an example of a histogram about the reference image information 80 and the captured image information 81. This histogram provides information acquired from such images captured by the first imaging unit 8 as shown in FIG. 3, that is, information represented by a graph with brightness on the abscissa and the number of pixels at each brightness value on the ordinate.

The reference image information 80 mainly has two peak values. One of them is a peak value at which the number of pixels is maximized on a high brightness side (denoted by reference sign B in FIG. 4), and the other is a peak value Iref at which the number of pixels is maximized on a low brightness side (denoted by reference sign D in FIG. 4). Low brightness-side image information having the peak value Iref is reference droplet image information 801. On the other hand, image information having a peak on the high brightness side is reference background image information 802 about the brightness of an image of a background other than the droplets. It is to be noted that a brightness value at the boundary between the side denoted by reference sign D and the side denoted by reference sign B may be appropriately set to any value.

Similarly, the captured droplet image information 81 of droplets imaged by the first imaging unit 8 also has two peak values. One of them is a peak brightness value at which the number of pixels is maximized on the high brightness side, and the other is a peak brightness value I at which the number of pixels is maximized on the low brightness side. Low brightness-side image information having the peak brightness value I is captured droplet image information 811. On the other hand, image information having a peak brightness value on the high brightness side is captured background image information 812 about the brightness of an image of a background other than the droplets.

At this time, the judgment unit 7 judges whether or not the peak brightness value I shifts with respect to the peak brightness value Iref. More specifically, as shown in FIG. 3, when droplets containing bubbles, foreign substances, or the like are imaged, an image concerning the captured droplet image information 811 is light-colored and blurred overall as compared to an image concerning the reference droplet image information 801. Therefore, the peak brightness value I shifts to the high brightness side with respect to the peak brightness value Iref.

Further, at this time, the judgment unit 7 preferably judges whether or not the peak brightness value I is within the range of Iref±i. The i is preferably about 10 to 30 when brightness has 256 gray levels in total. This makes it possible to more accurately detect the entry of bubbles, foreign substance, or the like.

Further, the judgment unit 7 judges whether or not the captured image information 81 is smaller in the number of pixels within the range of Iref±i by a predetermined value or more than the reference image information 80. The predetermined value is preferably about 25 to 50% of the number of pixels within the range in the reference image information 80, because the entry of bubbles, foreign substances, or the like can be more accurately detected.

On the other hand, the judgment unit 7 may judge whether or not the captured background image information 812 is smaller in the number of pixels within a predetermined range from the high brightness-side peak brightness value than the reference background image information 802. When the captured background image information 812 is smaller in this number of pixels than the reference background image information 802, it is judged that bubbles, foreign substances, or the like are contained in the droplets that have been imaged. The predetermined range is preferably about 5 to 10% of the number of pixels within a range in the reference background image information 80, because the entry of bubbles, foreign substances, or the like can be more accurately detected. In this manner, the presence of bubbles, foreign substances, or the like can be accurately detected by the judgment unit 7 based not only on the reference droplet image information 801 but also on the reference background image information 802.

When the judgment unit 7 judges that the captured image information 81 has changed with respect to the reference image information 80 in this manner, it is judged that bubbles, foreign substances, or the like have entered the particle sorting device 1 (Step S16). In this case, for example, the control unit 11 automatically stops sample sorting, or the notification unit 12 notifies a user of warning information. At this time, it is also possible to stabilize a flow channel by automatically sucking the sample through a suction port (not shown) provided in a laminar flow generation unit. On the other hand, when the judgment unit 7 judges that the captured image information 81 has not changed with respect to the reference image information 80, the particle sorting device 1 continues the sorting of droplets.

As described above, the use of the particle sorting device 1 according to this embodiment makes it possible to simply understand the presence of bubbles, foreign substances, or the like by comparison between the reference image information 80 and the captured image information 81 of droplets. Therefore, when bubbles, foreign substances, or the like are present, sample sorting can be stopped, and therefore, for example, clogging of a flow channel or the like caused by the entry of foreign substances can be prevented. This makes it possible to improve the stability or reliability of the particle sorting device 1. Further, when the particle sorting device 1 runs out of a sample set therein to be sorted so that bubbles are contained in droplets, the operation of sample sorting can be automatically stopped. This also makes it possible to improve the convenience of the particle sorting device 1. Further, the presence of bubbles or the like can be simply understood by the first imaging unit 8, which eliminates the necessity for separately providing a device such as a bubble detection sensor in the particle sorting device 1. This makes it possible to give the particle sorting device 1 greater structural freedom and to reduce production costs.

It is to be noted that the first embodiment has been described above with reference to a case where the microchip 2 is used, but the present disclosure is not limited thereto, and the same effects can be obtained even when a flow cell is used instead of the microchip 2.

<2. Second Embodiment>

Figure 5:
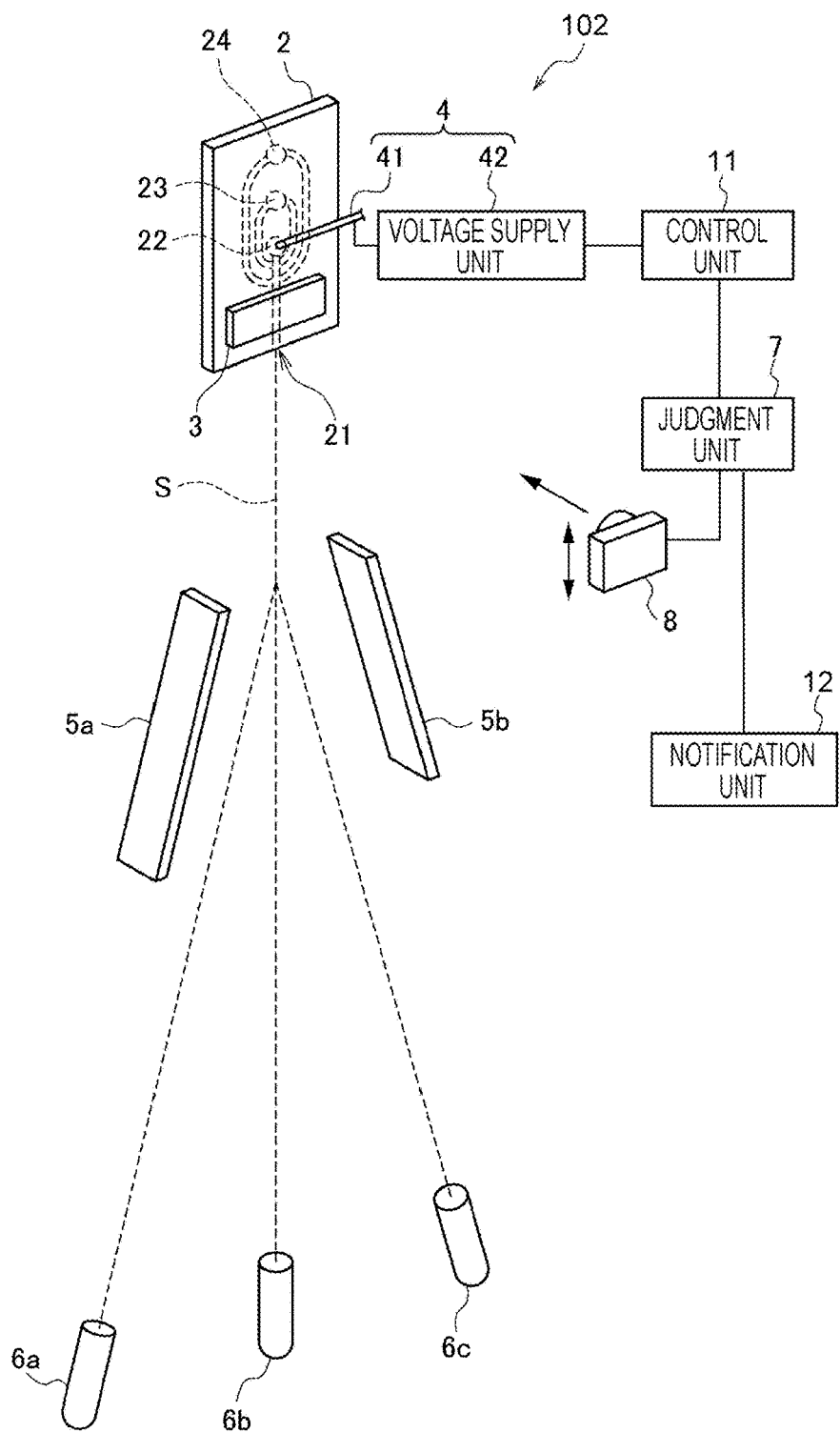
FIG. 5 is a schematic view showing an example of the structure of a particle sorting system 102 according to a second embodiment of the present disclosure.
Figure 6:
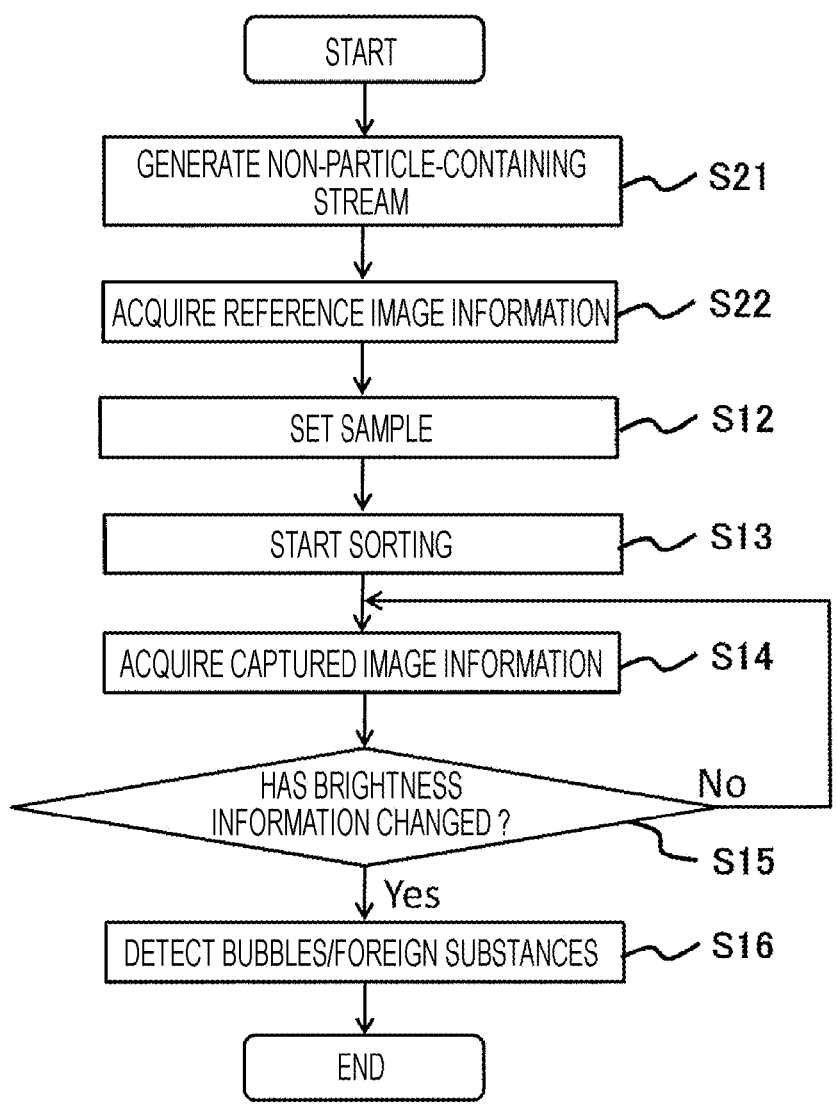
FIG. 6 is a flow chart showing the summary of a method for detecting bubbles, foreign substances, or the like with the use of the particle sorting device 102 according to this embodiment.

Hereinbelow, a particle sorting device 102 according to a second embodiment of the present disclosure will be described. FIG. 5 is a schematic view showing an example of the structure of the particle sorting device 102 according to the second embodiment of the present disclosure. FIG. 6 is a flow chart showing the summary of a method for detecting bubbles, foreign substances, or the like with the use of the particle sorting device 102 according to this embodiment. Bubbles, foreign substances, or the like often enter through the sample inlet 22, and therefore a stream containing no particle is often stable (i.e., droplets do not contain bubbles, foreign substances, or the like). The particle sorting device 102 according to this embodiment generates a stream containing no particle (non-particle-containing stream), and image information of droplets in this stream is used as the reference image information 80. Therefore, unlike the above-described first embodiment, the particle sorting device 102 according to this embodiment does not always need to read out data from the storage unit 10 in the step of detecting bubbles, foreign substances, or the like.

First, as shown in FIG. 6, the particle sorting device 102 according to this embodiment generates a non-particle-containing stream containing no particle (Step S21). Then, image information is acquired as the reference image information 80 by allowing the first imaging unit 8 to capture an image of droplets in the non-particle-containing stream (Step S22). At this time, the reference image information 80 may or may not be stored in the storage unit 10.

Then, a sample to be sorted is set, and the particle sorting device 102 judges whether or not bubbles, foreign substances, or the like are contained in a particle-containing stream in the same manner as the particle sorting device 1 according to the first embodiment (Steps S12 to S16). The features other than the above-described point and the effects of the particle sorting device 102 are also the same as those of the first embodiment according to the present disclosure.

As described above, the particle sorting device 102 according to this embodiment acquires, as the reference image information 80, image information of droplets in a non-particle-containing stream not containing bubbles, foreign substances, or the like before sample sorting. Therefore, it is not always necessary to read out the previously-stored reference image information 80 from the storage unit 10, which makes it possible to simply judge the presence of bubbles, foreign substances, or the like in droplets.

<3. Third Embodiment>

Figure 7:
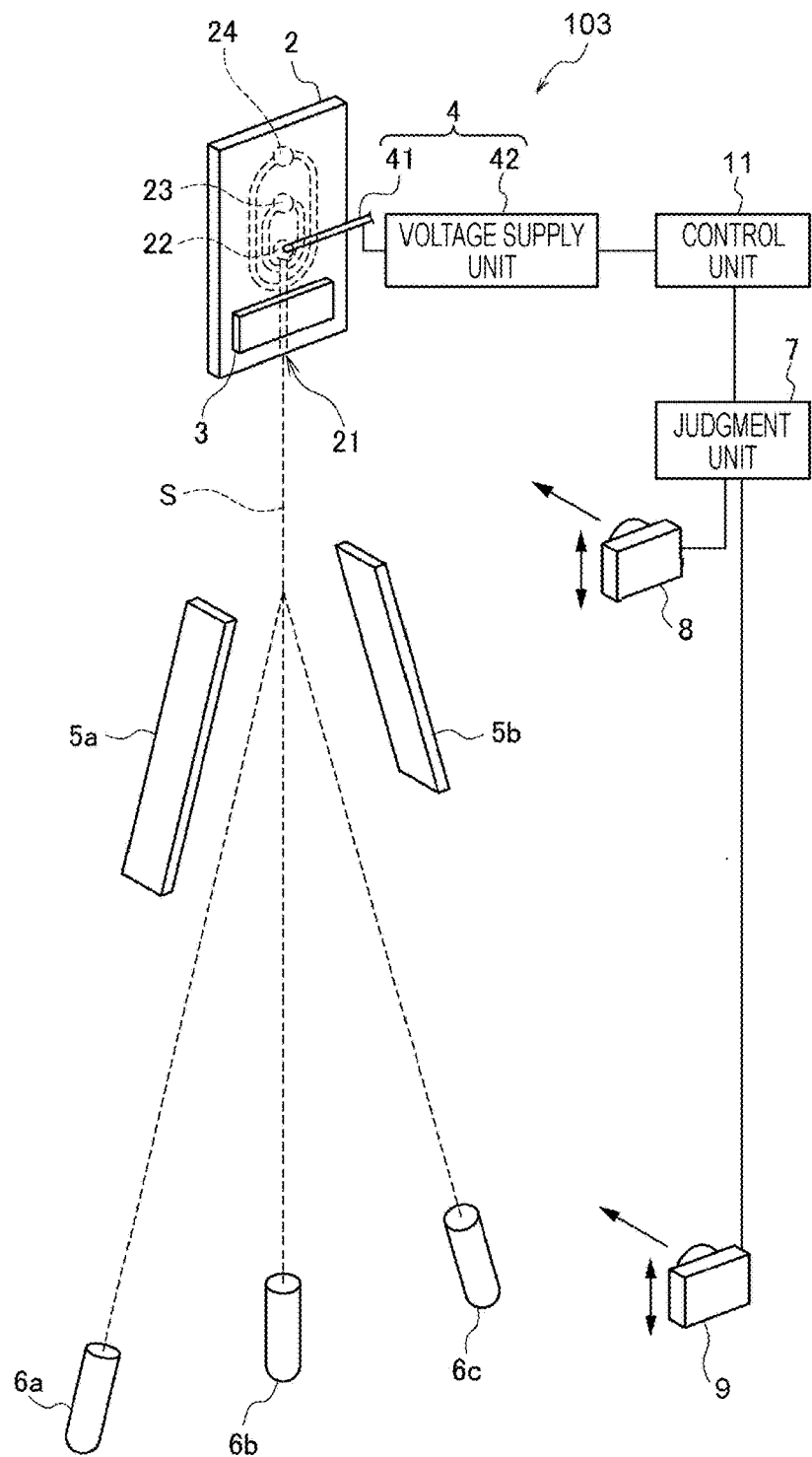
FIG. 7 is a schematic view showing an example of the structure of a particle sorting system 103 according to a third embodiment of the present disclosure.
Figure 8:
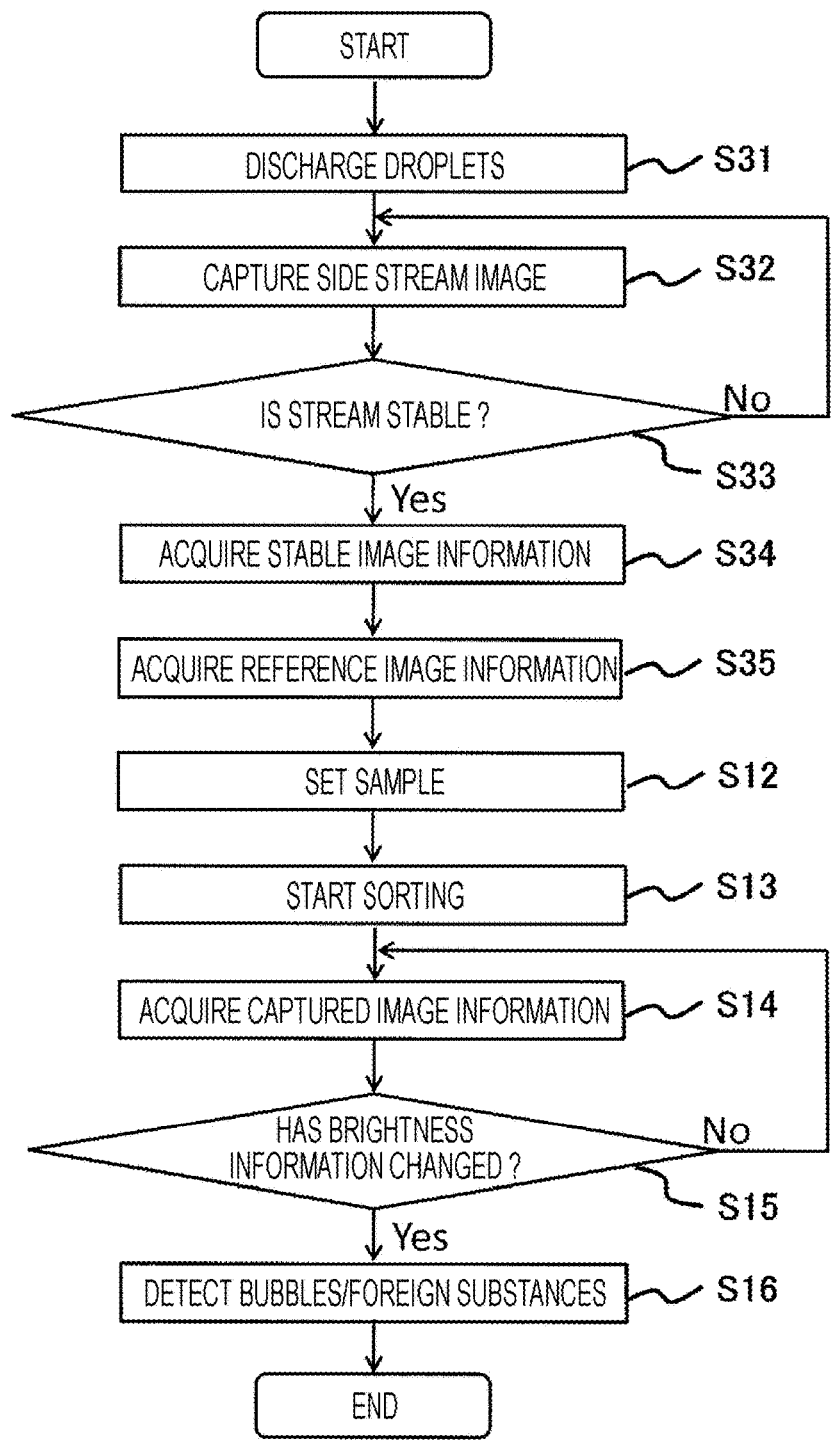
FIG. 8 is a flow chart showing the summary of a method for detecting bubbles, foreign substances, or the like with the use of the particle sorting device 103 according to this embodiment.

Hereinbelow, a particle sorting device 103 according to a third embodiment of the present disclosure will be described. FIG. 7 is a schematic view showing an example of the structure of the particle sorting device 103 according to the third embodiment of the present disclosure. FIG. 8 is a flow chart showing the summary of a method for detecting bubbles, foreign substances, or the like with the use of the particle sorting device 103 according to this embodiment.

As shown in FIG. 7, unlike the particle sorting device 1 according to the first embodiment and the particle sorting device 102 according to the second embodiment, the particle sorting device 103 according to this embodiment includes a second imaging unit (camera) 9 that captures an image of droplets that have passed through between the deflection plates 5a and 5b. In the particle sorting device 103 according to this embodiment, the second imaging unit 9 captures an image of a side stream to obtain second image information. When the second image information is stable image information, image information of the droplets acquired by the first imaging unit 8 is used as the reference image information 80.

It is to be noted that an image of the droplets can be captured not only by an imaging device such as a CCD or CMOS camera but also by any imaging element such as a photoelectric conversion element. The second imaging unit 9 may have a moving system for changing its position.

As shown in FIG. 8, the particle sorting device 103 first regularly applies a positive or negative electric charge to droplets to generate a side stream (Step S31). Each of the droplets in this side stream may or may not contain a particle. Then, the second imaging unit 9 captures an image of the side stream that has passed through between the deflection plates 5a and 5b to acquire second image information (Step S32).

Figure 9:
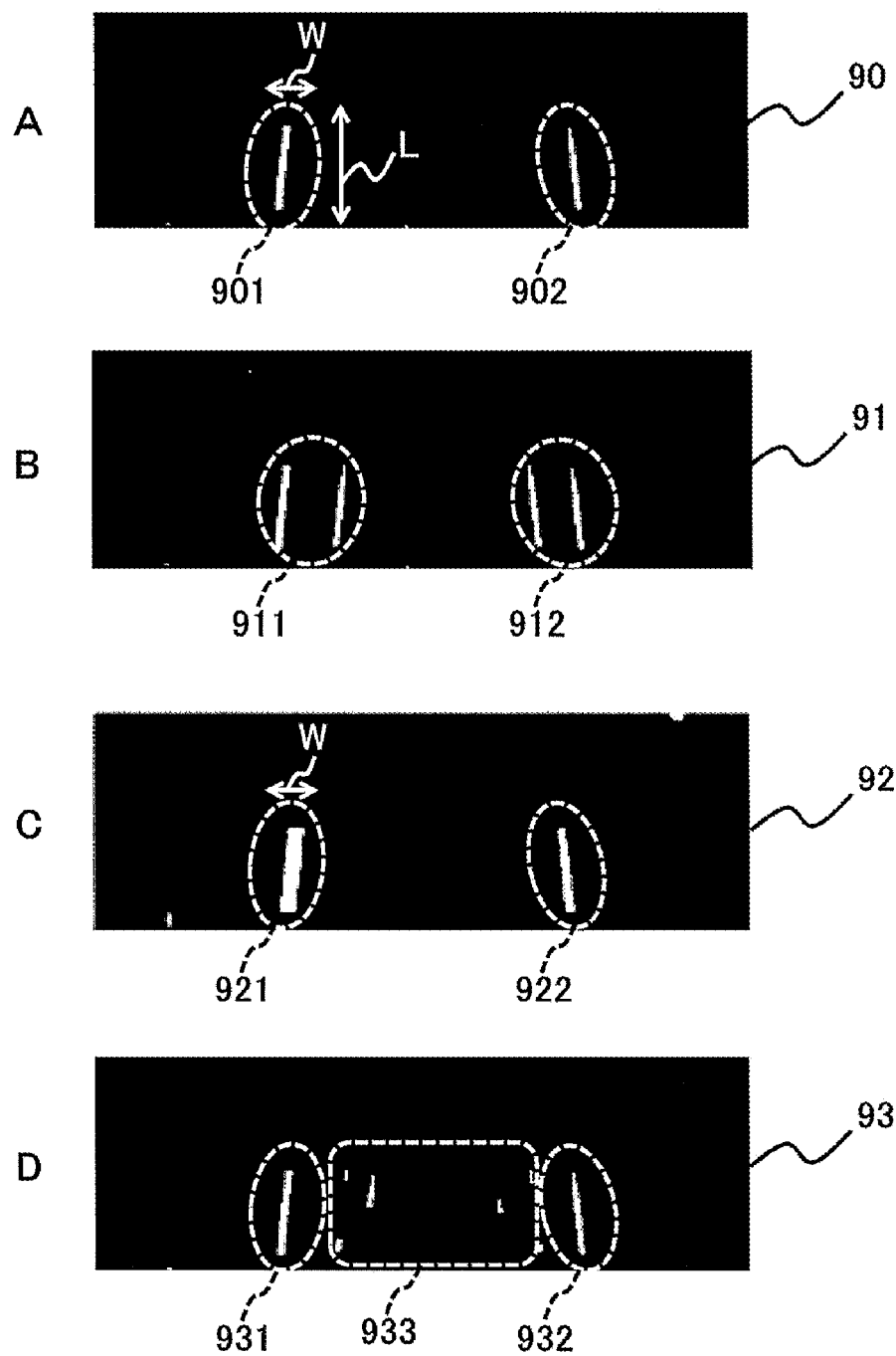
FIGS. 9A to 9D show examples of images captured by a second imaging unit 9.

FIG. 9 shows examples of images captured by the second imaging unit 9, wherein image information shown in FIG. 9A is stable image information 90, and image information shown in FIGS. 9B to 9D is unstable image information 91 to 93. As shown in FIG. 9A, when images 901 and 902 concerning the side stream are each one linear image whose length in the direction in which the stream is formed is, for example, equal to or larger than an arbitrarily set length L and whose width is, for example, equal to or less than an arbitrarily set width W, the judgment unit 7 judges that the image information is judged as stable image information 90. The ratio of the length L to the width W (L/W) may be appropriately set to fall in a predetermined preferred range. Then, the judgment unit 7 judges that the droplets do not contain bubbles, foreign substances, or the like, and image information of the droplets acquired by the first imaging unit 8 can be used as the reference image information 80 (Steps S33 and S34).

On the other hand, as shown in FIG. 9B, when images 911 and 912 concerning the side stream each include two or more linear images, the judgment unit 7 judges that the image information is unstable image information 91, and image information of the droplets acquired by the first imaging unit 8 is not used as reference image information. Further, as shown in FIG. 9C, also when images 921 and 921 concerning the side stream each have a width equal to or larger than an arbitrarily set width W, the judgment unit 7 judges that the image information is unstable image information 92. Further, as shown in FIG. 9D, also when an image 933 whose number of pixels is equal to or larger than an arbitrarily set value N is captured in addition to linear images 931 and 932 of the side stream, the judgment unit 7 judges that the image information is unstable image information 93.

As described above, when the side stream is stable so that the stable image information 90 can be acquired, image information of the droplets acquired by the first imaging unit 8 is used as the reference image information 80 (Step S35 in FIG. 8). At this time, the reference image information 80 may or may not be stored in the storage unit 10. On the other hand, when the unstable image information 91 is acquired, the second imaging unit 9 continues to capture an image of the side stream until stable image information is acquired.

Then, a sample to be sorted is set, and the particle sorting device 103 judges whether or not bubbles, foreign substances, or the like are contained in droplets of the sample in the same manner as the particle sorting devices 1 and 102 according to the first and second embodiments (Steps S12 to S16). The features other than the above-described point and the effects of the particle sorting device 103 are also the same as those of the first and second embodiments of the present disclosure.

As described above, the particle sorting device 103 according to this embodiment uses, as the reference image information 80, image information of droplets forming a stable side stream, and therefore can more accurately and simply judge the presence of bubbles, foreign substances, or the like in droplets.

<4. Fourth Embodiment>

Hereinbelow, a particle sorting system according to a fourth embodiment of the present disclosure will be described. In the particle sorting system according to this embodiment, analysis by the judgment unit 7 is performed by a device different from the particle sorting device 1, 102, or 103 according to the first, second, or third embodiment that performs particle sorting and detection. The particle sorting device 1, 102, or 103 and the device (not shown) including the judgment unit 7 may be, for example, directly connected through a server or connected so as to be able to intercommunicate through a network. It is to be noted that the particle sorting system according to this embodiment has the same features and effects as the particle sorting device 1, 102, or 103 according to the first, second, or third embodiment of the present disclosure except that the judgment unit 7 is provided in a device different from the particle sorting device.

Further, the present disclosure may provide the following.

(1)

A particle sorting device including a judgment unit that judges whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

(2)

The particle sorting device according to the above (1), wherein the reference image information includes the reference droplet image information and reference background image information about a brightness of an image of a background other than the droplets, whose peak brightness value is higher than that of the reference droplet image information, and the captured image information includes the captured droplet image information and captured background image information about a brightness other than the droplets, whose peak brightness value is higher than that of the captured droplet image information.

(3)

The particle sorting device according to the above (2), wherein the judgment unit judges whether or not the peak brightness value of the captured droplet image information is higher than the peak brightness value of the reference droplet image information.

(4)

The particle sorting device according to the above (2) or (3), wherein the judgment unit judges whether or not the captured droplet image information is smaller in a number of pixels within a predetermined range of brightness from the peak brightness value of the droplet image in the reference droplet image information than the reference droplet image information.

(5)

The particle sorting device according to any one of the above (2) to (4), wherein the judgment unit judges whether or not the captured droplet image information is smaller in a number of pixels within a predetermined range of brightness from the peak brightness value of the image other than the droplets in the reference image information than the reference droplet image information.

(6)

The particle sorting device according to any one of the above (1) to (5), including a charge unit that applies an electric charge to at least some of droplets discharged from the orifice, deflection plates that are provided so as to be opposed to each other across a fluid stream formed by the droplets to change a traveling direction of the droplets, and a first imaging unit that captures an image of the droplets at a position where a fluid discharged from the orifice is converted into droplets to generate the reference image information and the captured image information.

(7)

The particle sorting device according to any one of the above (1) to (6), further including a storage unit that stores the reference image information.

(8)

The particle sorting device according to any one of the above (1) to (6), wherein the reference image information is image information including an image of droplets containing no particle.

(9)

The particle sorting device according to the above (6), further including a second imaging unit that captures an image of the droplets that have passed through between the deflection plates, wherein the judgment unit judges whether or not second image information of the droplets acquired by the second imaging unit is previously-set stable image information, and wherein when the second image information is the stable image information, image information of the droplets about the second image information captured by the first imaging unit is determined as the reference image information.

(10)

The particle sorting device according to any one of the above (1) to (9), further including a notification unit that notifies a user of warning information when the captured image information has changed with respect to the reference image information.

(11)

The particle sorting device according to any one of the above (1) to (10), further including a control unit that automatically stops sorting of particle-containing droplets when the captured image information has changed with respect to the reference image information.

(12)

A method for analyzing particles, including the step of allowing a judgment unit to judge whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

(13)

A program which allows a particle sorting device to perform a function of judging whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

(14)

A particle sorting system including a judgment unit that judges whether or not captured image information including captured droplet image information about a brightness of an image of particle-containing droplets captured after discharge from an orifice has changed with respect to previously-set reference image information including reference droplet image information about a brightness of an image of droplets captured after discharge from the orifice.

REFERENCE SIGNS LIST 1, 102, 103 Particle sorting device
2 Microchip
3 Vibrating element
4 Charge unit
5a, 5b Deflection plate
6a-6c Recovery container
7 Judgment unit
8 First imaging unit
9 Second imaging unit
10 Storage unit 11 Control unit
12 Notification unit
21 Orifice
22 Sample inlet
23 Sheath inlet
24 Suction outlet
41 Electrode
42 Voltage supply unit
50 Reference image information
81 Captured image information
90 Stable image information
801 Reference droplet image information
802 Reference background image information
811 Captured background image information
812 Captured droplet image information
S Fluid stream

The invention claimed is:

1. A particle sorting device comprising:
a flow channel and an orifice providing an opening at an end of the flow channel;
a vibrating element arranged to apply a micro vibration to a liquid flowing through the flow channel to convert a fluid discharged from the orifice into droplets; and
a judgment unit adapted to:
analyze histogram data prepared from captured image information and from previously-set reference image information, wherein the captured image information is obtained from an image having droplets discharged from the orifice and wherein the histogram data identifies a number of pixels having a brightness level for a plurality of different brightness levels associated with the captured image information;
determine whether or not the captured image information, which includes captured droplet image information about a brightness of an image of particle-containing droplets captured after discharge from an orifice, has changed with respect to the previously-set reference image information, which includes reference droplet image information about a brightness of an image of droplets captured after discharge from the orifice, based on changes in one or more peaks in the histogram data; and
evaluate operation of the droplet sorter based on determining whether or not the captured image information has changed with respect to the previously-set reference image information.

2. The particle sorting device according to claim 1, wherein
the reference image information includes the reference droplet image information and reference background image information about a brightness of an image of a background other than the droplets, whose peak brightness value is higher than that of the reference droplet image information, and
the captured image information includes the captured droplet image information and captured background image information about a brightness other than the droplets, whose peak brightness value is higher than that of the captured droplet image information.

3. The particle sorting device according to claim 2, wherein the judgment unit judges whether or not the peak brightness value of the captured droplet image information is higher than the peak brightness value of the reference droplet image information.

4. The particle sorting device according to claim 2, wherein the judgment unit judges whether or not the captured droplet image information is smaller in a number of pixels within a predetermined range of brightness from the peak brightness value of the droplet image in the reference droplet image information than the reference droplet image information.

5. The particle sorting device according to claim 2, wherein the judgment unit judges whether or not the captured droplet image information is smaller in a number of pixels within a predetermined range of brightness from the peak brightness value of the image other than the droplets in the reference image information than the reference droplet image information.

6. The particle sorting device according to claim 1, comprising
a charge unit that applies an electric charge to at least some of droplets discharged from the orifice,
deflection plates that are provided so as to be opposed to each other across a fluid stream formed by the droplets to change a traveling direction of the droplets, and
a first imaging unit that captures an image of the droplets at a position where a fluid discharged from the orifice is converted into droplets to generate the reference image information and the captured image information.

7. The particle sorting device according to claim 6, further comprising a storage unit that stores the reference image information.

8. The particle sorting device according to claim 6, wherein the reference image information is image information including an image of droplets containing no particle.

9. The particle sorting device according to claim 6, further comprising
a second imaging unit that captures an image of the droplets that have passed through between the deflection plates, wherein
the judgment unit judges whether or not second image information of the droplets acquired by the second imaging unit is previously-set stable image information, and wherein
when the second image information is the stable image information, image information of the droplets about the second image information captured by the first imaging unit is determined as the reference image information.

10. The particle sorting device according to claim 1, further comprising a notification unit that notifies a user of warning information when the captured image information has changed with respect to the reference image information.

11. The particle sorting device according to claim 1, further comprising a control unit that automatically stops sorting of particle-containing droplets when the captured image information has changed with respect to the reference image information.

12. A method for analyzing particles, including:
receiving captured image information obtained from imaging droplets discharged from an orifice, wherein the droplets are produced by a vibrating element arranged to apply a micro vibration to a liquid flowing through a flow channel to convert a fluid discharged from the orifice at the end of the flow channel into the droplets;
analyzing histogram data prepared from the captured image information and from previously-set reference image information obtained from a droplet sorter, wherein the captured image information is obtained from an image having droplets discharged from the orifice and wherein the histogram data identifies a number of pixels having a brightness level for a plurality of different brightness levels associated with the captured image information;

determining whether or not the captured image information, which includes captured droplet image information about a brightness of an image of particle-containing droplets captured after discharge from an orifice, has changed with respect to the previously-set reference image information, which includes reference droplet image information about a brightness of an image of droplets captured after discharge from the orifice, based on changes in one or more peaks in the histogram data; and evaluating operation of the droplet sorter based on determining whether or not the captured image information has changed with respect to the previously-set reference image information.

13. Non-transitory computer-readable medium encoding instructions that, when executed, adapt a particle sorting device to perform acts of:

receiving captured image information obtained from imaging droplets discharged from an orifice, wherein the droplets are produced by a vibrating element arranged to apply a micro vibration to a liquid flowing through a flow channel to convert a fluid discharged from the orifice at the end of the flow channel into the droplets;

analyzing histogram data prepared from the captured image information and from previously-set reference image information obtained from a droplet sorter, wherein the captured image information is obtained from an image having droplets discharged from the orifice and wherein the histogram data identifies a number of pixels having a brightness level for a plurality of different brightness levels associated with the captured image information;

judging whether or not the captured image information, which includes captured droplet image information about a brightness of an image of particle-containing droplets captured after discharge from an orifice, has changed with respect to the previously-set reference image information, which includes reference droplet image information about a brightness of an image of droplets captured after discharge from the orifice, based on changes in one or more peaks in the histogram data; and evaluating operation of the droplet sorter based on determining whether or not the captured image information has changed with respect to the previously-set reference image information.

14. A particle sorting system comprising:

a flow channel and an orifice providing an opening at an end of the flow channel;

a vibrating element arranged to apply a micro vibration to a liquid flowing through the flow channel to convert a fluid discharged from the orifice into droplets; and a judgment unit adapted to:

analyze histogram data prepared from captured image information and from previously-set reference image information obtained from a droplet sorter, wherein the captured image information is obtained from an image having droplets discharged from the orifice and wherein the histogram data identifies a number of pixels having a brightness level for a plurality of different brightness levels associated with the captured image information;

determine whether or not the captured image information, which includes captured droplet image information about a brightness of an image of particle-containing droplets captured after discharge from an orifice, has changed with respect to the previously-set reference image information, which includes reference droplet image information about a brightness of an image of droplets captured after discharge from the orifice, based on changes in one or more peaks in the histogram data; and evaluate operation of the droplet sorter based on determining whether or not the captured image information has changed with respect to the previously-set reference image information.

* * * * *